United States Patent [19]
Flumene et al.

[11] Patent Number: 5,364,360
[45] Date of Patent: Nov. 15, 1994

[54] NEEDLE FOR MEDICAL USE WITH SAFETY PROTECTION

[76] Inventors: Antonio G. Flumene, Via Garavetti, 6; Giuseppe Pilo, Via Muroni, 22, both of 07100 Sassari, Italy

[21] Appl. No.: 94,158
[22] PCT Filed: Jan. 25, 1992
[86] PCT No.: PCT/EP92/00156
  § 371 Date: Jul. 28, 1993
  § 102(e) Date: Jul. 28, 1993
[87] PCT Pub. No.: WO92/14502
  PCT Pub. Date: Sep. 3, 1992

[30] Foreign Application Priority Data
Feb. 19, 1991 [IT] Italy .................. MI91A000422

[51] Int. Cl.5 ................................ A61M 5/00
[52] U.S. Cl. .......................... 604/110; 604/198; 604/263
[58] Field of Search .............. 604/110, 198, 192, 263, 604/187

[56] References Cited
U.S. PATENT DOCUMENTS

| | | | |
|---|---|---|---|
| 4,826,490 | 5/1989 | Byrne et al. | 604/110 X |
| 5,011,479 | 4/1991 | Le et al. | 604/198 |
| 5,098,403 | 3/1992 | Sampson | 604/198 |
| 5,181,524 | 1/1993 | Wanderer et al. | 604/198 X |

*Primary Examiner*—John D. Yasko
*Attorney, Agent, or Firm*—Wegner, Cantor, Mueller & Player

[57] ABSTRACT

A needle is provided with a protective cap which is substantially cylindrical in shape and has one open end and an opposed tapered end having a central hole through which the needle can emerge. The cap has a diameter so that in use it can slide onto a cylindrical body which carries the needle.

15 Claims, 5 Drawing Sheets

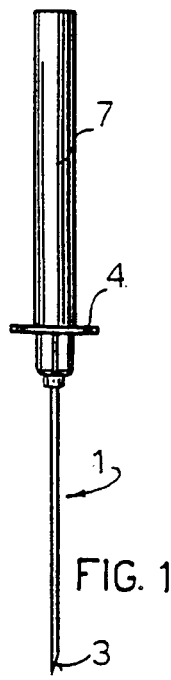
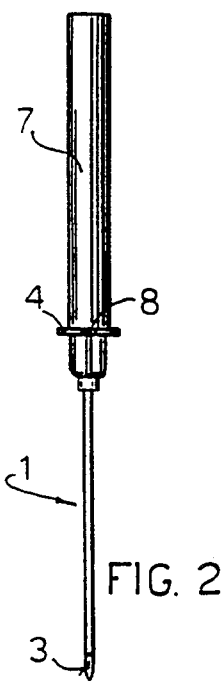
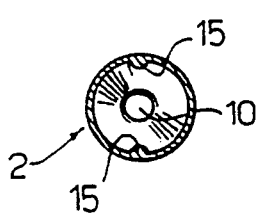
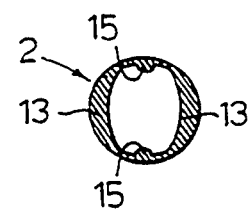
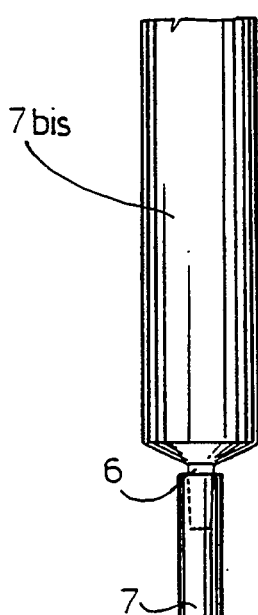
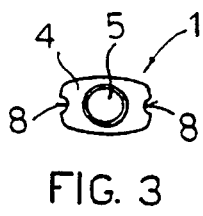
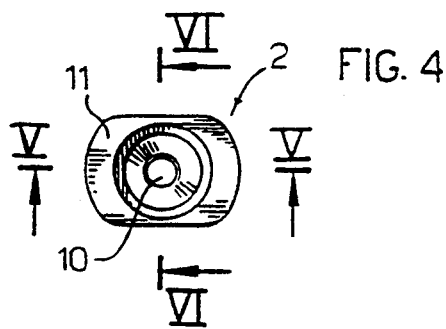
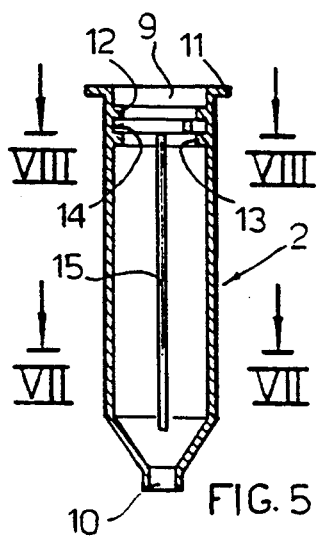
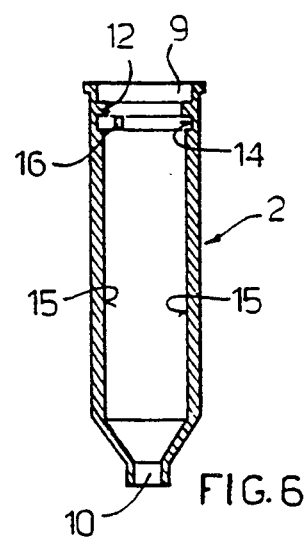
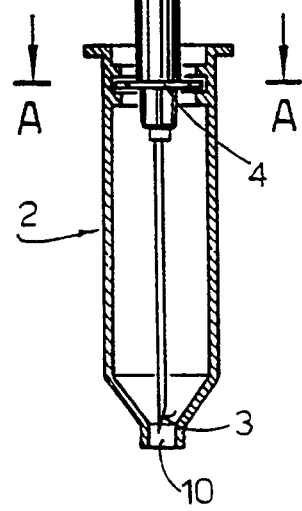

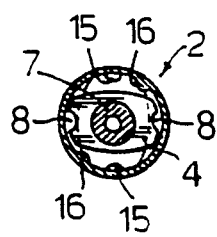
FIG. 10
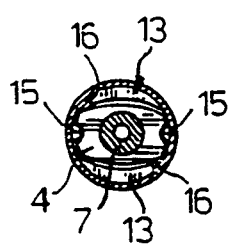
FIG. 11
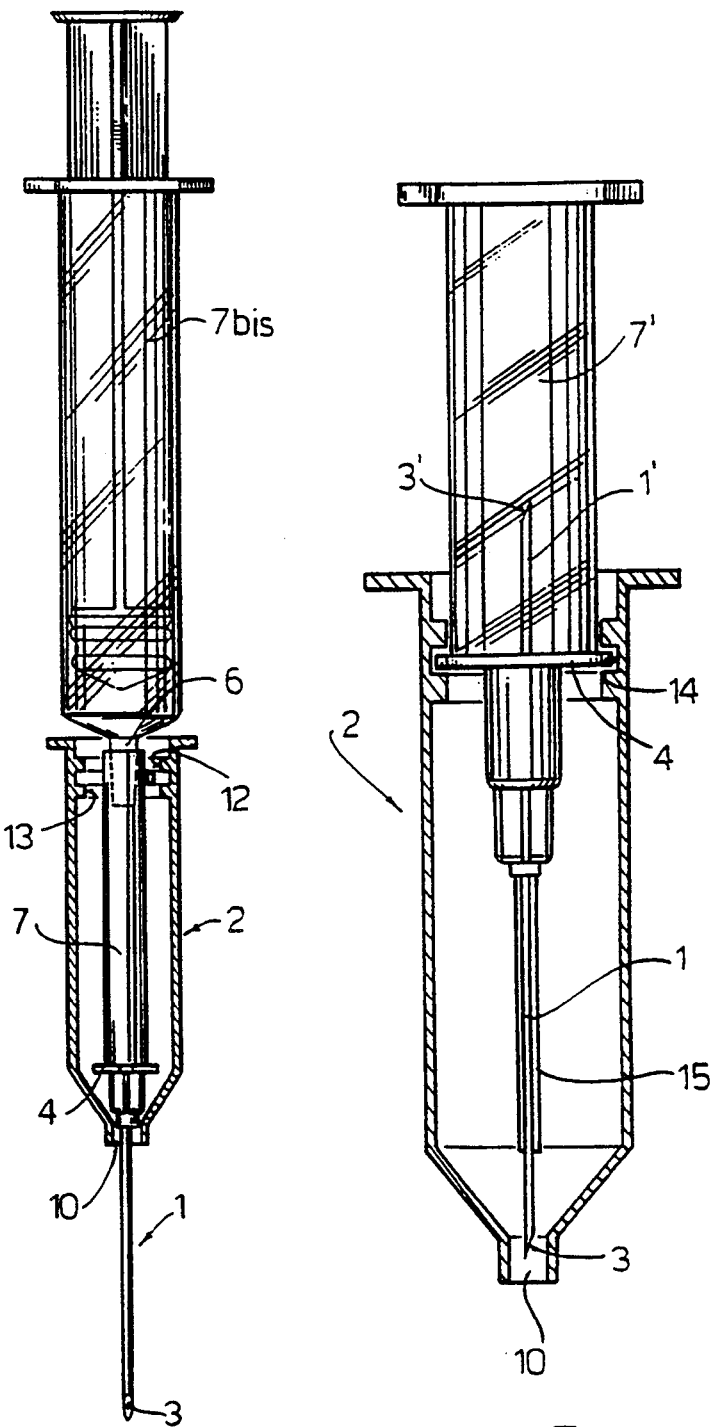
FIG. 12
FIG. 13

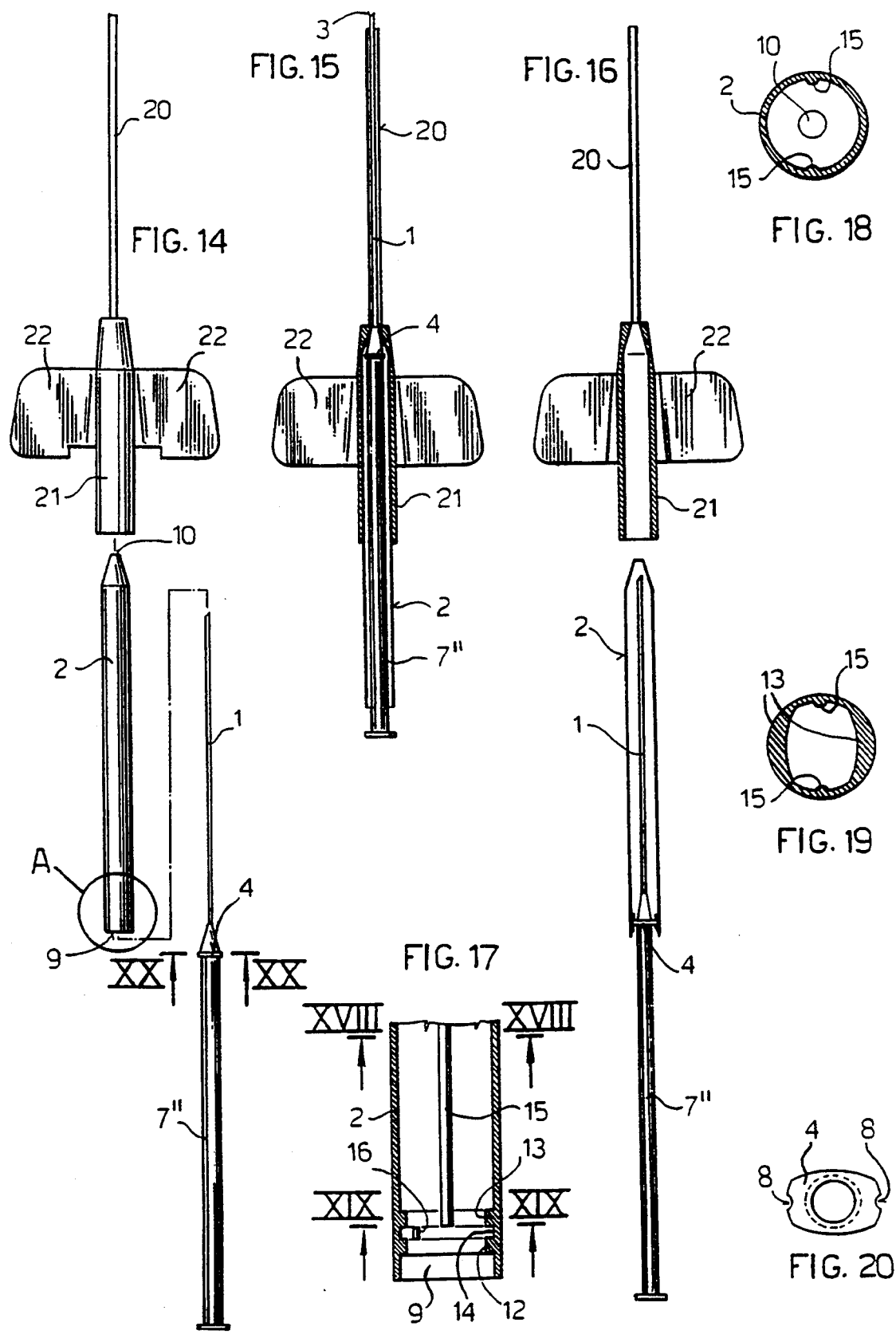

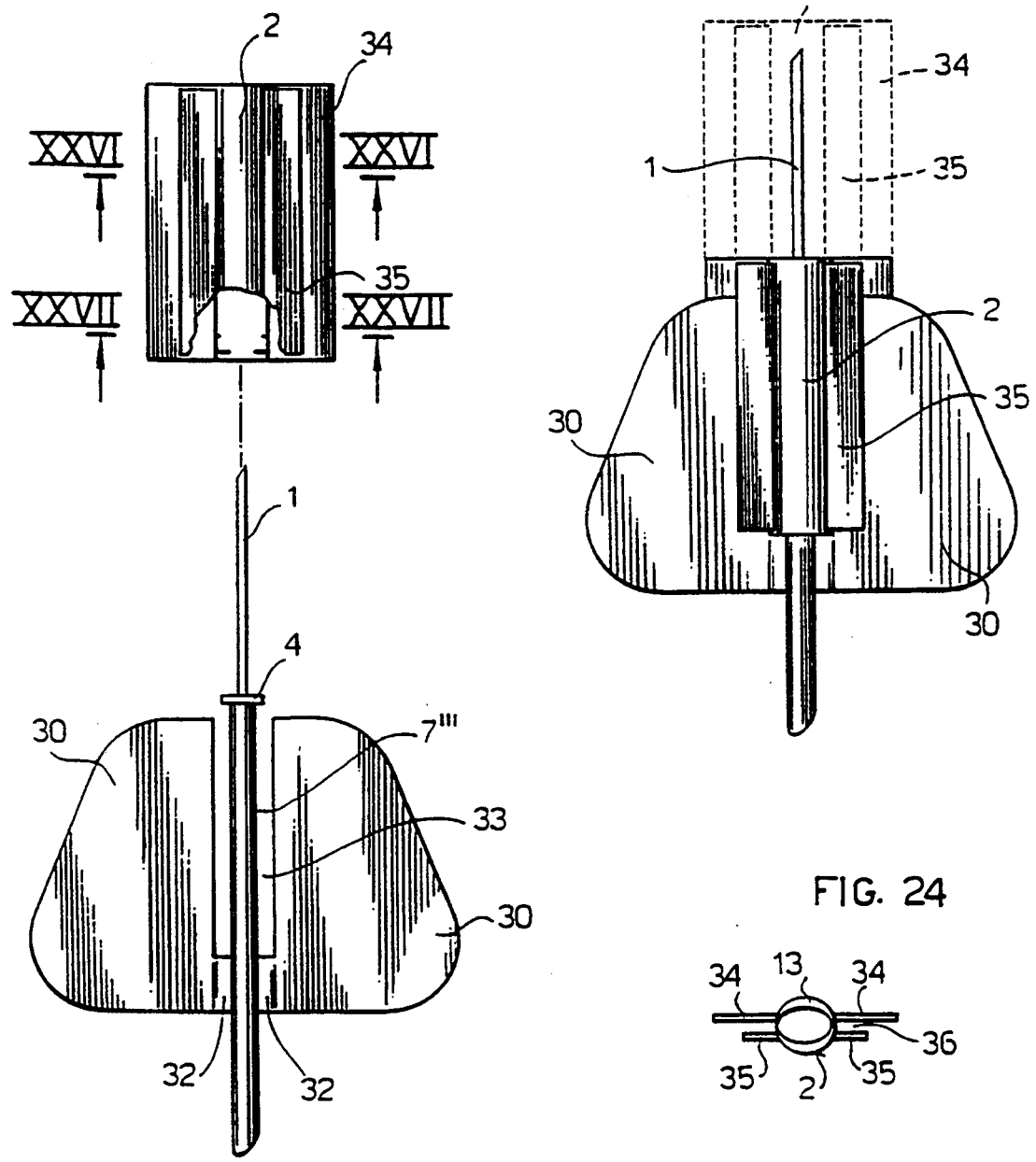
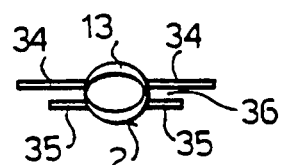
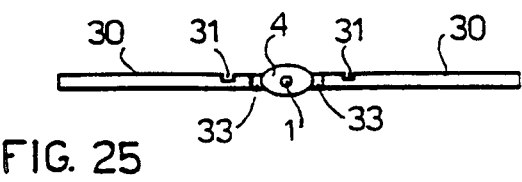

NEEDLE FOR MEDICAL USE WITH SAFETY PROTECTION

The present invention refers to a needle for syringes, for drawing samples with a vacuum test-tube for endovasal and similar uses, having a safety protection, suitable for eliminating any danger of wounding after use.

As is already known, the throw-away needles which exist on the market are usually applied to the corresponding syringes and are covered by a protective cap, which is slid oaf at the moment they are used.

The cap, which is substantially cylindrical or slightly conical in shape, with an opening at the wider end, must be replaced in position on the needle after the injection has been made, and this is necessary obviously to avoid leaving the needle uncovered, which could wound, for instance, the refuse collection staff.

Since the opening of the protective cap of the needle is relatively small, there exists a risk of the needle not centring it when it is being reinserted into the cap, and consequently wounding the user. This can happen at any time, simply through carelessness but more probably through the tiredness of the medical or paramedical staff at the end of a hospital duty shift.

The danger of the user being wounded is a major problem today, considering the existence of diseases, some of them fatal, such as the acquired immunity deficiency syndrome (AIDS), which are transmitted through being pricked by infected needles.

In order to eliminate or at least avoid any danger of wounding when covering the needle after the syringe has been used, it has already been suggested to foresee a protective cap of the needle, which can be adjusted from a rest position, in which it completely covers the needle, to a use position, in which it places itself around the syringe, thus exposing the needle. After the injection has been made the cap can be slid onto the needle again.

Such a method is known for example from U.S. Pat. No. A-4,968,304, wherein the needle and the related cap are usually separated by the syringe, the connection of the needle with the syringe taking place by means of a screw mounting. A closing plug is provided on the cap, which must be removed before use and replaced after use. During such operations there always exists the risk of the user to be wounded.

A similar method is disclosed in U.S. Pat. No. A-4,961,730 which foresees elastic means, in correspondence with the base of the needle, co-operating with the inner surface of the cap, suitably shaped, to obtain the locking of the needle inside the cap.

This solution which is quite complicated, expensive and difficultly feasible, does not allow a completely safe locking of the needle due to the presence of said elastic means.

Both methods disclosed in U.S. Pat. No. A-4,968,304 and U.S. Pat. No. A-4,961,730 are specifically conceived for hypodermic syringe needles so that their application to needles for different uses, such as cannula-needles or butterfly needles for endovasal use, is hardly envisageable.

FR-A-2 620 942 describes a syringe for dental use, wherein a protective cap is provided on the needle, which is brought over the syringe body during the use. Also in this case it cannot be envisaged an application of the protective cap For other kinds of needle.

The aim of the invention is to eliminate the drawbacks set forth above and revolutionize the solution proposed in the aforementioned prior arts, providing an extremely simple, cheap and safe method to protect the needle, which applies to whatsoever kind thereof.

The aim is achieved, according to the invention, by means of the features listed in the characterizing portion of the attached claim 1.

Advantageous embodiments of the invention are disclosed in the dependent claims.

In particular, according to a modified embodiment, the needle can be used for drawing samples with vacuum test-tubes in place of syringes.

According to the known art, For this type of application two opposed needles with respective protective caps are foreseen. One of such needles is intended to be inserted into the vein while the other is for inserting into a vacuum test-tube, in which the blood is collected. At the base of the latter needle a threaded tang is foreseen, onto which a tubular element is screwed at the moment of use. In this application, the same problems arise as those described for syringes.

According to this embodiment of the invention, a cylindrical sleeve is foreseen at the opposite part of the needle point, which is enbloc with the base and encloses a second needle which Forms an extension of the first, the protective cap being moved on said sleeve during use. After use, the cap is replaced on the first needle, as in the case of the needle for syringes, while the second needle still remains protected by the coupling.

In a second modified embodiment the needle is a cannula-needle endovasal use, e.g. to administer fluids or for similar uses.

A cannula-needle is made of a metallic guide needle or "mandrel" enclosed in a flexible plastic material cannula. During use the whole is inserted in the vein as a common needle, then the metallic guide needle is extracted, for example to connect the cannula with a phleboclysis to be dripped to the patient. During such an operation there exists the risk of the user to be wounded.

According to this modified embodiment of the invention the protective cap is placed between the guide needle and the cannula, more precisely between a cylindrical handle of the guide needle and a tubular support of the cannula, the guide needle being housed in said cap while it is being extracted, and is locked in it after rotation, as in the preceding cases. The guide needle and the cap can be thus removed enbloc from the cannula and thrown in a refuse collector for the further disposal without risk of wounding.

In a third modified embodiment the needle is a butterfly needle, always for endovasal use.

As known, a butterfly needle has, in correspondence with the base, two opposite flexible wings, intended to facilitate its introduction in the vein and the subsequent locking, and carries a rear connecting little tube.

According to this modified embodiment of the invention, the two wings are fixed to the base or needle body only for a short part, so as to allow the insertion between them of the protective cap which is placed on the needle, after use, and locked by means of rotation. In this application two opposite coupled blades forming respective guides for the sliding of the butterfly needle wings ere suitably provided on the cap in substitution for the longitudinal guides usually foreseen on the cap.

Further characteristics of the invention will be more clearly understood from the detailed description given below, which refers to its purely exemplary and therefore not restrictive embodiments, illustrated in the appended drawings, in which:

FIG. 1 is a side elevation of a needle for syringes according to the invention;

FIG. 2 is a view of the needle in FIG. 1, rotated through 90°;

FIG. 3 is a top plan view of the needle;

FIG. 4 is a top plan view of the protective cap of the needle;

FIGS. 5 and 6 are median sections of the cap taken according to lines V—V and VI—VI respectively in FIG. 4;

FIGS. 7 and 8 are transverse sections of the cap taken along lines VII—VII and VIII—VIII respectively in FIG. 5;

FIG. 9 is a median sectional view of the cap, complete with needle, applied to a syringe, before the cap is slid off;

FIGS. 10 and 11 are transverse sectional views taken along line A—A in FIG. 9, with the cap shown in two positions, rotated through 90° with respect to each other;

FIG. 12 is a view like the one in FIG. 9, with the cap carried on the tubular support of the needle, which is ready for use;

FIG. 13 shows, partially in view and partially in median section, a first modified embodiment of the needle with the safety protection according to the invention, usable for taking samples with a vacuum test-tube;

FIG. 14 is an exploded schematic view of a second modified embodiment of the invention concerning a cannula-needle;

FIG. 15 is a view of the cannula-needle in FIG. 14 in an assembled position.

FIG. 16 is a view of the guide needle extracted from the cannula and protected by the cap.

FIG. 17 is an enlarged section of the cap end, indicated by A in FIG. 14, substantially corresponding to the section of FIG. 5;

FIG. 18 is a section, taken along line XVIII—XVIII of FIG. 17, equal to the section of FIG. 7;

FIG. 19 is a section, taken along line XIX—XIX of FIG. 17, equal to the section of FIG. 8;

FIG. 20 is a view along line XX—XX of FIG. 14 equal to the view of FIG. 3;

FIG. 21 is an exploded view of a third modified embodiment relevant to the butterfly needle;

FIG. 22 is a view of the butterfly needle in FIG. 21 ready for use.

FIGS. 24 and 25 are top views of the sole cap and of the sole butterfly needle respectively;

Figure 27:
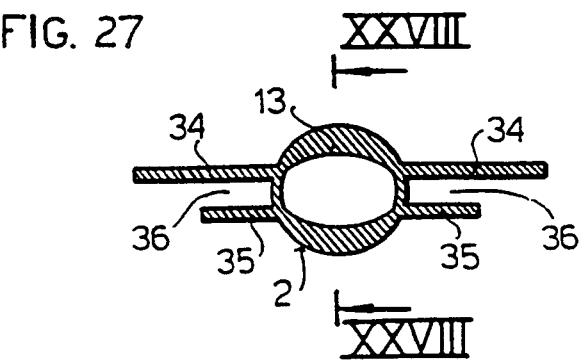
FIGS. 26 and 27 are sectional views taken along lines XXVI—XXVI and XXVII—XXVII in FIG. 21.
Figure 26:
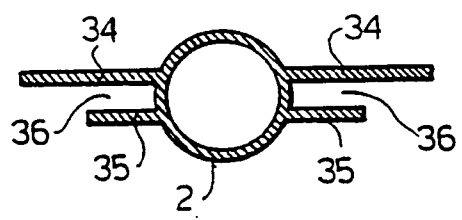

With reference to such figures, and starting with the figures from 1 to 12, reference numbers 1 and 2 show respectively the needle and the related protective cap according to the invention.

The needle 1 is a perfect ordinary needle for a syringe, having a point 3 and a base 4 at the opposite end, from which a tubular support 7 projects, with a central hole 5 intended for housing the tang 6 of the syringe 7bis (see in particular FIGS. 9 and 12). The differences with respect to a traditional needle are represented by the shape of the base 4, which is widened and substantially oval, with two opposed notches 8, the purpose of which will be described below, and by the tubular support 7 at the back of the base 4.

The cap 2 has a substantially cylindrical form, with an internal diameter which enables it to slide onto the tubular support 7 (FIG. 12), and it has an open end 9 and the other end tapered with a central opening 10 for the needle 1 to emerge. A flange 11 can be foreseen in correspondence with the opening 9, to make it easier to hold.

Near the opening 9, inside the cap 2, a continuous or broken annular projection 12 is foreseen, which forms a ledge suitable for preventing the needle emerging from the opening 9.

Below the stop collar 12 two opposed half-moon projections 13 are foreseen, in such a way that a seating 14 is defined between the collar 12 and the projections 13, intended for housing the base 4 of the needle 1.

Inside the cap 2 two opposed longitudinal guides 15 are also foreseen, capable of engaging with the notches 8 foreseen on the base 4 of the needle 1, to guide the sliding of the cap 2.

In the seating 14 for the base 4 of the needle, two teeth 16 can be foreseen, acting as stops for the rotation of the cap 2 with respect to the needle I or viceversa.

The needle 1 is inserted into the protective cap 2 during the production phase, by making it pass over the annular projection 12 at the base 4 by means of heating and/or pressure.

The needle and the related protective cap are then packed in a sealed bag and sold separately or already applied to the syringe 7, as shown in FIG. 9, and packed together with the latter.

During use, if the needle 1 has not been applied to the syringe 7bis yet, the tang 6 of the syringe is inserted into the hole 5 of the tubular support 7 of the base 4 of the needle, as shown in FIG. 9.

In such a position, the base 4 of the needle 1 is positioned so that it is locked between the upper annular projection 12 and the lower projections 13. Then the cap 2 is rotated, through an angle of about 90°, for example, so as to bring the opposed guides 15 in line with the notches 8 of the base 4 of the needle (FIG. 11). Centring the notches 8 can be facilitated by correctly locating the teeth 16 foreseen in the seating 14. The cap 2 can then be slid off upwards, in the opposite direction from the point 3 of the needle 1, and position itself around the tubular support 7, remaining integral with the latter temporarily through the slight interference which exists between at least one of the projections 12 and 13 and the outer surface of the tubular body itself, as shown in FIG. 12.

After the injection has been made—an operation which is not in the least impeded by the cap 2—the cap 2 is once more slid downwards in order to cover the needle 1, until the base 4 of the needle positions itself in the seating 14, after which the cap 2 is rotated in the opposite direction from the previous one, so as to bring the base 4 to engage with the half-moon projections 13, and therefore prevent the possibility of the needle sliding out of its own accord.

At this point, since the syringe 7bis is usually of the throw-away type, it is thrown into the appropriate containers together with the needle and the related protection.

If, however, for any reason, it is desired to remove the needle from the syringe, this can be done easily by exercising traction on the cap 2 and rotating it further so that the engagement of the teeth 16 with the base 4 of the needle 1 produces a rotation of the latter, and therefore makes it easier to disconnect the tang 6 of the syringe, as, in fact, takes place in the case of needles of the traditional type.

From what has been described, it is easy to see the advantages of the needle with its related protective cap according to the invention, which can be applied to a syringe of any size, without varying the size of the cap 2 and, consequently, the size of the base 4 of the needle 1.

As an alternative to what has been shown in FIGS. 1 to 12, the needle 1 can be made without the rear tubular support 7 and the cap have a larger diameter so as to be carried directly on the syringe 7bis.

A description is now given of the modified embodiments of the invention keeping the same references used in the previous figures to indicate the same parts, and adding a prime to the references which indicate parts which are similar.

FIG. 13 shows a needle for drawing samples with vacuum test-tubes.

As can be seen in such figure, the only difference with respect to the needle for syringes illustrated in FIGS. 1 to 12 consists, in substitution for the tubular support 7, in the presence of a second needle 1' with a point 3', on axis and in opposition to the main needle 1. The needle 1', which is usually shorter than the needle 1, projects from the centre of the base 4, which in this case obviously does not have the central hole 5.

Likewise, from the base 4, in the same direction as the second needle 1', a cylindrical sleeve 7' projects, which encloses the needle 1', and on which the cap 2 is positioned during use.

In fact, during use, the needle 1 is inserted into the vein, and the needle 1' is inserted into a vacuum test-tube, which is housed in the cylindrical sleeve 7', for collecting the blood.

The needle protection system in FIG. 13 is therefore exactly the same as that of the needle illustrated in the figures from 1 to 12.

The modified embodiment shown in FIGS. 14 to 20 relates to a cannula-needle which, as known, comprises a guide needle or mandrel provided with a rear cylindrical handle 7" and a cannula 20 surrounding the needle 1 and having at its back a tubular body 21 partially housing the handle 7" of the needle.

Two opposed wings 22 intended for example to lock the cannula on the patient's skin by means of plasters are foreseen on the body 21.

According to the invention the handle 7" of the needle is suitably lengthened and the protecting cap 2, completely similar in its structure to the cap of FIGS. 4–8, is placed between it and the tubular body 21 of the cannula.

The cannula-needle is packed in the assembled condition of FIG. 15, or possibly with the metallic guide needle or mandrel 1 slightly retracted, in such a way that its point 3 does not project beyond the end of the cannula 20.

During use the needle 1 is inserted in a vein or in an artery causing the contemporary insertion of the cannula 20. Then the needle 1 is retracted acting on its cylindrical handle 7", keeping the cap in the position of FIG. 15, i.e. housed in the tubular body 21 of the cannula 20. A coupling with a slight interference between the cap 2 and the tubular body 21 can be also foreseen. When the needle is completely retracted so as to be entirely housed in the cap 2, that is when its base or collar 4 positions itself in the seating 14 of the cap, a rotation through about 90° is carried out to lock it in that position. The guide needle 1 and the cap 2 can be thus slid off from the cannula, as shown in FIG. 16, and thrown in a refuse collector for the further disposal thereof without risk of wounding.

A connector, for example to drip a phleboctysis to a patient, can be then connected to the end of the tubular body 21. A further connector could be possibly foreseen at a side of the body 21.

A description is now given of the modified embodiment shown in FIGS. 21 to 28, relevant to a butterfly needle for endovasal use comprising a needle 1 with a tubular body 7''' in correspondence of which two opposed flexible wings 30 are foreseen to facilitate the introduction of the needle into the vein and the subsequent locking of the same by means of plasters.

A little tube is connected to the back of the body 7''', in a known way, to drip for example a phleboclysis to the patient.

The flexibility of the wings 30 is obtained by means of weakening ribs 31 (see in particular FIG. 25).

According to the invention the wings 30 are fixed to the body 7''' only by a short rear part 32 so as to form long slits 33 for the insertion between them of the protective cap 2.

When packed, the cap 2 can be placed in the position shown by dotted lines in FIG. 22 and brought, during use, in the position shown by unbroken lines in the same figure.

In alternative, the cap 2 can be placed during packaging in the position shown by unbroken lines in FIG. 22, any auxiliary little plastic tube being foreseen to protect the needle 1.

Figure 23:
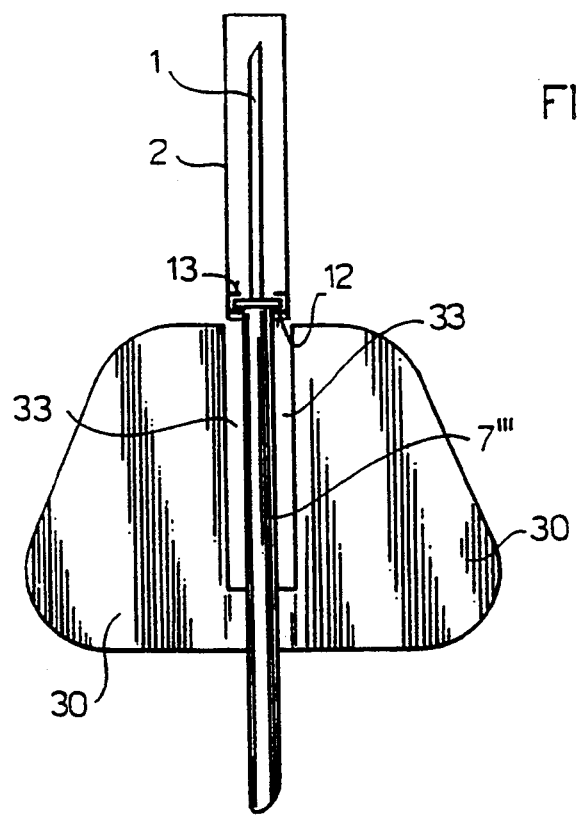
FIG. 23 is a view of the butterfly needle after being used with the cap covering the needle.
Figure 28:
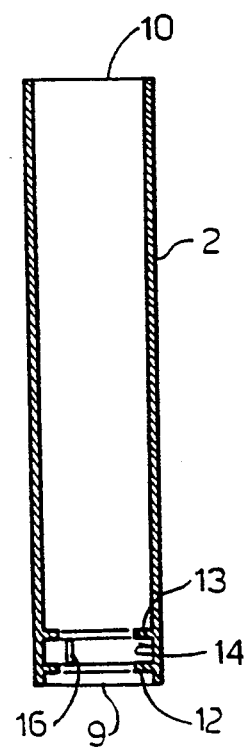
FIG. 28 is a section taken along line XXVIII—XXVIII in FIG. 27.

After it has been used the cap 2 is slid off onto the needle 1 until its base or collar 1 is inserted in the housing 14 foreseen inside the cap 2. The cap is then rotated through about 90° and locked in such a position (FIG. 23).

According to this embodiment pairs of opposed wings 34, 35, preferably different in length, are foreseen outside the cap 2 to determine corresponding seatings 36 to house the wings 30 of the butterfly needle. In this way the longitudinal sliding guides 15, which are foreseen in the cap 2 according to the preceding embodiments, can be eliminated.

We claim:

1. A needle for medical use, provided with a protective cap (2) substantially cylindrical in shape, with one open end (9) and an opposite opening (10), the diameter of the cap (2) being such that it can slide on a cylindrical body provided at the back of the needle to move from a needle covering position to a position in which the needle is uncovered and vice versa, wherein said cylindrical body (7, 7', 7", 7''') is integral with the needle (1) and inside the cap (2), near the open end (9) a seating (14) is provided, suitable for receiving a substantially oval widened base or collar (4) of the needle (1), the seating (14) being limited at the top by a continuous or broken annular projection (12) forming an insurmontable ledge for the base of the needle, and at the bottom by two opposed "half-moon" projections (13), shaped in such a way as to allow the base (4) of the needle (1) to pass, after correct positioning.

2. A needle according to claim 1, wherein inside the said seating (14) at least one tooth (6) is provided, acting as a stop for the rotation of the cap (2) with respect to the base (4) or vice versa.

3. A needle according to claim 1, wherein on the base (4) of the needle (1) at least one notch (8) is provided, suitable for engaging with a corresponding longitudinal guide (15) provided inside the cap (2) for a guided sliding between the needle and the cap.

4. A needle according to claim 1 wherein at least the projection (12) or the projections (13), or both, have dimensions such that they interfere slightly with the outer surface of the cylindrical body (7, 7', 7'', 7'''), so as to make the cap (2) integral with the cylindrical during use.

5. A needle according to claim 1 wherein the said opening (10) is made centrally at a tapered end of the cap (2).

6. A needle according to claim 1 wherein said cylindrical body is a tubular support (7) at the back of the base (4) and integral with the needle (1) for connection to a tang (6) of a syringe (7bis) (FIGS. 1-12).

7. A needle according to claim 1 wherein said cylindrical body is a sleeve (7') integral with the needle (1) and encloses a second needle (1') disposed axially with the needle (1) (FIG. 13).

8. A needle according to claim 1 wherein said needle (1) is the guide needle or mandrel of a cannula needle, and wherein said cylindrical body is a handle (7'') of the guide needle (1) and the cap (2) is located between said handle (7'') and a tubular body (21) of the cannula (20) (FIGS. 14-20).

9. A cannula-needle according to claim 8, wherein two flexible wings (22) are provided outside said tubular body (21).

10. A needle according to claim 1 wherein said cylindrical body is the body (7''') of a butterfly needle, provided with two flexible opposed wings (30), said wings (30) being fixed to the body (7''') of the needle (1) only by a short rear part (32), so as to define longitudinal slits (33) for the insertion between them of the protective cap (2) (FIGS. 21-28).

11. A butterfly needle according to claim 10, wherein pairs of opposed wings (34, 35) forming seats (36) are provided on said cap (2) to house and make the wings (30) of the butterfly needle (1) slide.

12. A butterfly needle according to claim 11, wherein said wings (34, 35) are different in length.

13. A needle according to claim 1 which is packed in a sealed bag together with the related protective cap (2).

14. A syringe for injections, which is provided with a needle (1) with a related protective cap (2), according to claim 1.

15. A needle according to claim 3, wherein the base of the needle is provided with at least two opposed notches.

* * * * *